(12) United States Patent
Williams et al.

(10) Patent No.: US 11,191,589 B2
(45) Date of Patent: Dec. 7, 2021

(54) MICROWAVE ABLATION APPLICATORS

(71) Applicant: Gyrus Medical Limited, Cardiff (GB)

(72) Inventors: David Nicholas Williams, Caerphilly (GB); Tudor Thomas, Cardiff (GB)

(73) Assignee: Gyrus Medical Limited, Cardiff (GB)

( * ) Notice: Subject to any disclaimer, the term of this patent is extended or adjusted under 35 U.S.C. 154(b) by 0 days.

(21) Appl. No.: 15/870,814

(22) Filed: Jan. 12, 2018

(65) Prior Publication Data
US 2018/0214205 A1  Aug. 2, 2018

(30) Foreign Application Priority Data
Jan. 27, 2017  (GB) ..................................... 1701364

(51) Int. Cl.
*A61B 18/18* (2006.01)
*A61B 18/00* (2006.01)

(52) U.S. Cl.
CPC . *A61B 18/1815* (2013.01); *A61B 2018/00011* (2013.01); *A61B 2018/00023* (2013.01); *A61B 2018/00744* (2013.01); *A61B 2018/00779* (2013.01); *A61B 2018/00791* (2013.01); *A61B 2018/183* (2013.01); *A61B 2018/1861* (2013.01); *A61B 2018/1869* (2013.01); *A61B 2018/1892* (2013.01)

(58) Field of Classification Search
CPC ...... A61B 18/1815; A61B 2018/00011; A61B 2018/00744; A61B 2018/00779; A61B 2018/00791; A61B 2018/183; A61B 2018/1861; A61B 2018/00005; A61B 2018/00023; A61B 2018/1838; A61B 2018/1869; A61B 2018/1892

USPC .......... 606/33; 607/101, 104, 105, 113, 115, 607/154, 156
See application file for complete search history.

(56) References Cited

U.S. PATENT DOCUMENTS

| | | | | |
|---|---|---|---|---|
| 5,281,217 | A | * | 1/1994 | Edwards ................ A61B 18/18 606/41 |
| 2007/0027449 | A1 | * | 2/2007 | Godara .............. A61B 18/1482 606/41 |
| 2008/0135217 | A1 | * | 6/2008 | Turovskiy .............. A61B 18/18 165/104.33 |

(Continued)

FOREIGN PATENT DOCUMENTS

| EP | 2474341 A1 | 7/2012 |
|---|---|---|
| WO | WO-96/18349 A2 | 6/1996 |

(Continued)

OTHER PUBLICATIONS

Davies, Geraint, "UK Search Report", prepared for application No. 1701364.0, dated May 30, 2017, 7 pages.

*Primary Examiner* — Thomas A Giuliani
(74) *Attorney, Agent, or Firm* — Winstead PC

(57) ABSTRACT

A shaft assembly for a microwave ablation applicator which includes a shaft assembly and an antenna assembly located within the shaft assembly is disclosed. The shaft assembly comprises an elongate shaft which extends from a first end to a second end thereof, and which defines therein a hollow inner volume and a longitudinal axis of the antenna assembly, and an applicator tip mounted on the second end of the elongate shaft. The shaft assembly further includes a coolant delivery tube having a side wall which defines an elongate hollow interior.

8 Claims, 4 Drawing Sheets

(56) References Cited

U.S. PATENT DOCUMENTS

| | | | |
|---|---|---|---|
| 2011/0077635 A1* | 3/2011 | Bonn | A61B 18/18 606/33 |
| 2012/0239019 A1* | 9/2012 | Asconeguy | A61B 18/1492 606/33 |
| 2013/0012940 A1 | 1/2013 | Desinger et al. | |
| 2014/0276743 A1* | 9/2014 | Curley | A61B 18/1815 606/33 |
| 2016/0051327 A1 | 2/2016 | Brannan | |

FOREIGN PATENT DOCUMENTS

| WO | WO-2007/006158 A1 | 1/2007 |
|---|---|---|
| WO | WO-2016/054156 A1 | 4/2016 |

\* cited by examiner

MICROWAVE ABLATION APPLICATORS

CROSS-REFERENCE TO RELATED APPLICATIONS

This patent application claims priority from, and incorporates by reference the entire disclosure of, UK Patent Application GB 1701364.0 filed on Jan. 27, 2017.

The present invention relates to microwave ablation applicators, and, in particular, to shaft assemblies for such applicators.

BACKGROUND OF THE INVENTION

In the treatment of tumours, for example tumours caused by a disease such as cancer, it is known to use microwave ablation techniques to ablate the tumour. Such microwave ablation techniques typically ablate the targeted tissue by delivering a controlled amount of microwave energy into the tumour.

Minimally-Invasive techniques for delivering such microwave energy have been shown to be effective in the treatment of tumours. In a minimally-invasive technique, a microwave emitter is inserted directly into a point of treatment, either using a normal shaft orifice or via percutaneous insertion. Such minimally-invasive procedures and devices provide a means of treating tumours in patients who either cannot undergo other forms of treatment (e.g. radiotherapy, surgical resection, chemotherapy) or where ablation is preferred as a therapy.

The microwave emitter is provided in a microwave ablation applicator. One type of commonly used microwave ablation applicator has an elongate shaft assembly that houses an antenna assembly. The shaft assembly is provided by a shaft in the form of a thin walled cylinder which extends from a proximal end to a distal end thereof and defines an inner volume therein, and an applicator tip which is carried by, and closes, the distal end of the shaft. The applicator tip has a shape which is appropriate for insertion in to the tissue being treated, and which provides suitable electromagnetic properties. One particular exemplary antenna assembly includes a dipole antenna element located towards the distal end of the shaft in the inner volume of the shaft, adjacent the applicator tip. The antenna assembly also includes a coaxial conductor which extends along the inner volume of the shaft in order to connect the dipole antenna element to a source of microwave energy.

It is desirable for a microwave ablation applicator to be narrow and lightweight, but with high stiffness. For this reason, composite fibre-resin materials (fibre reinforced plastics, FRP, materials) have been considered as appropriate for the shaft. However, some fibre reinforced plastics materials result in undesirably thick side walls for the shaft leading to an undesirably large overall outer diameter of the shaft. Conversely, a desirably narrow shaft of the same material would result in lower than required stiffness of the shaft. Carbon fibre reinforced plastics (CFRP) materials enable the provision of a narrower side wall, and hence narrower shaft overall, due to the higher strength and stiffness of a CFRP material compared with other FRP materials. However, CFRP materials contain carbon fibres that are electrically conductive, and are, therefore, not suitable for attachment to an electrically conductive tip of the antenna assembly, since the conductivity of the carbon would prevent radiation of microwave energy from the applicator tip.

It is, therefore, desirable to provide a shaft assembly that is able to address the drawbacks of the previously-considered designs.

SUMMARY OF THE INVENTION

According to a first aspect of the present invention, there is provided a shaft assembly for a microwave ablation applicator which includes a shaft assembly and an antenna assembly located within the shaft assembly, the shaft assembly comprising an elongate shaft which extends from a first end to a second end thereof, and which defines therein a hollow inner volume and a longitudinal axis of the antenna assembly, an applicator tip mounted on the second end of the elongate shaft, and a coolant delivery tube having a side wall which defines an elongate hollow interior, the coolant delivery tube extending along the inner volume of the shaft, coaxial therewith, the coolant delivery tube having a first end towards the first end of the shaft for reception of coolant fluid therein, and a second end towards, and spaced from, the second end of the shaft, the second end of the coolant tube providing a first fluid flow path from the interior of coolant tube into the inner volume of the shaft adjacent the applicator tip, wherein the coolant delivery tube defines a return aperture through the side wall thereof, which return aperture is of a fixed size and is located between the first and second ends of the coolant delivery tube within the elongate shaft, and which return aperture provides a second fluid flow path from the interior of the coolant delivery tube into a return volume of the inner volume of the shaft, which second fluid flow path is spaced apart from the second end of the coolant delivery tube.

In one example, the coolant delivery tube defines a plurality of such return apertures through the side wall thereof. In one such example, the return apertures are spaced apart circumferentially around the side wall of the coolant delivery tube. In another example, the return apertures are arranged in a plane substantially perpendicular to the longitudinal axis of the shaft.

DETAILED DESCRIPTION OF THE PREFERRED EMBODIMENTS

Figure 1:
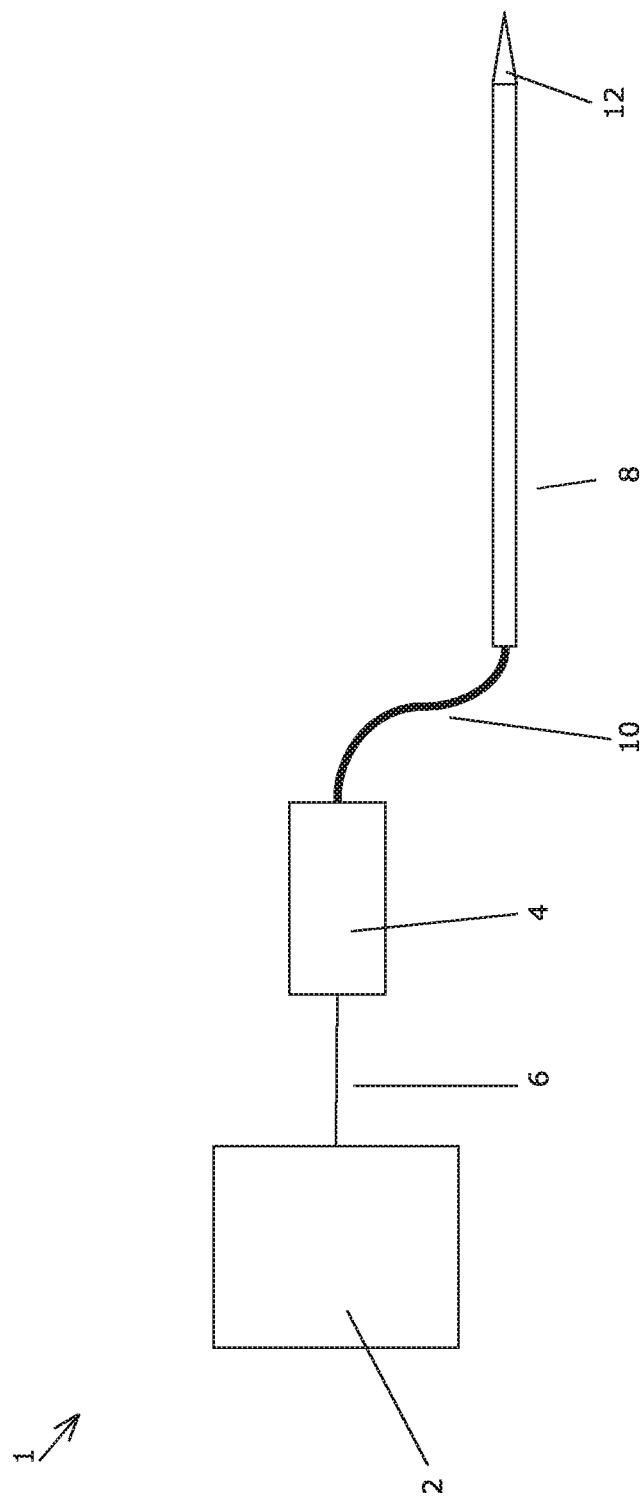
FIG. 1 is a schematic block diagram of a microwave ablation system.

FIG. 1 is a schematic diagram illustrating a microwave ablation system 1 comprising a controller unit 2, and a microwave power generator 4 which is connected to the controller via a control connection 6. An ablation applicator 8 is connected to the microwave power generator 4 via a power connection 10. The ablation applicator 8 includes a shaft assembly having a shaft which carries an applicator tip 12 which aids insertion of the ablation applicator 8 into the tissue being treated, and enables a desired output pattern of microwave energy from the ablation applicator 8.

The controller unit 2 is operable to control the power generator 4 to supply the correct magnitude and frequency of microwave energy to the ablation applicator 8. Different control schemes are known in the art, and will not be described here for the sake of clarity. The present invention is concerned with the design of the ablation applicator 8, and such an as ablation applicator 8 may be used with any appropriate control scheme and control hardware.

Figure 2:
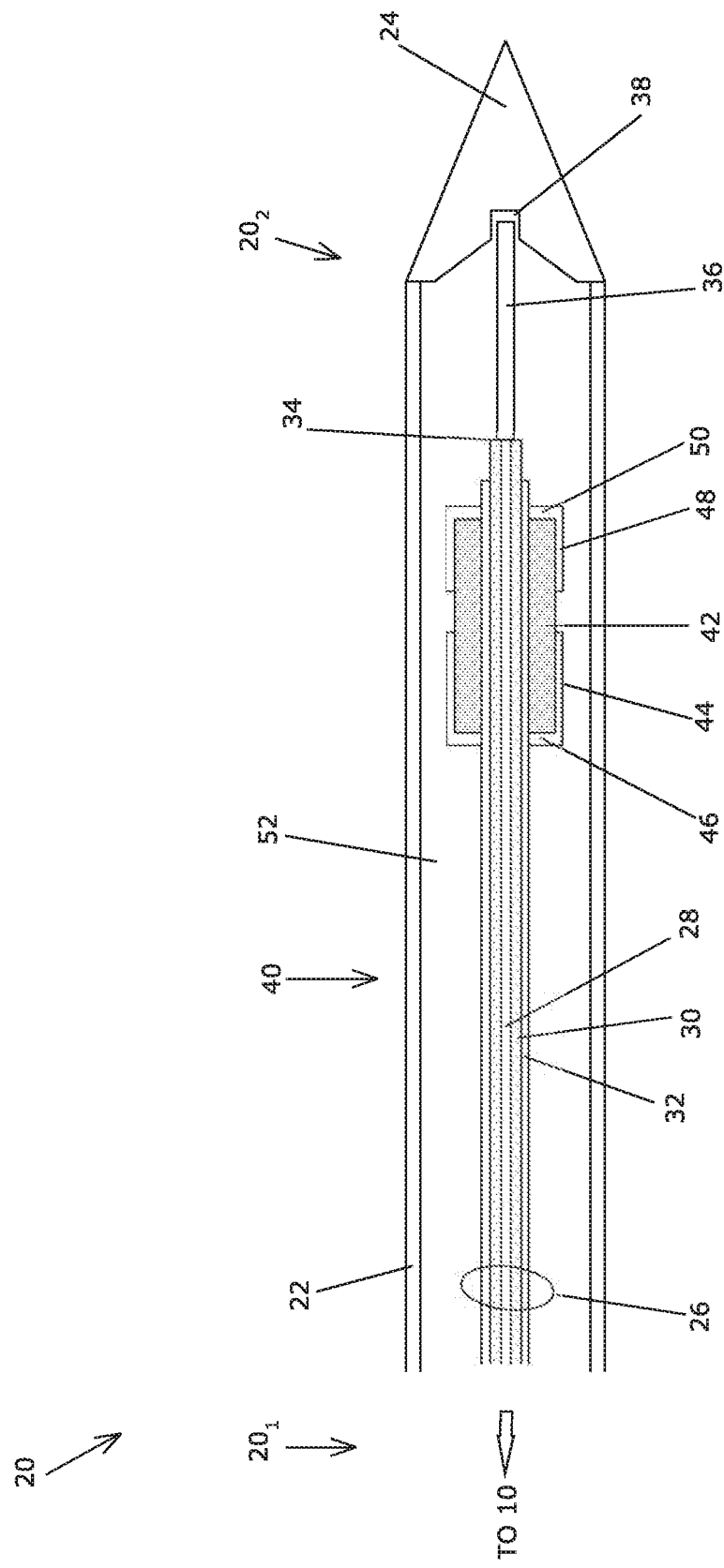
FIG. 2 is a cross sectional side view of part of a microwave ablation applicator.

FIG. 2 is a cross-sectional view of part of an ablation applicator 20 which comprises a shaft assembly and an antenna assembly. The shaft assembly includes a shaft 22, preferably cylindrical in form, which extends from a first (proximal) end $20_1$ to a second (distal) end $20_2$, and defines a longitudinal axis of the assembly and applicator. The second (distal) end $20_2$ of the shaft carries an applicator tip 24 for insertion into the tissue being treated. The shaft 22 defines an inner volume, in which most of the other components of the applicator are housed. The shaft 22 provides the applicator with the necessary rigidity for insertion into the tissue being treated. The shaft 22 is of a substantially rigid composite material, and is typically 1.5 to 3 mm in diameter.

The shaft assembly includes an applicator tip 24 which is attached to the second end $20_2$ of the shaft 22, so as to close off the inner volume at the second end. The applicator tip 24 is preferably a faceted trocar and has a relatively sharp distal end point. The applicator tip 24 is designed to be suitable for insertion into the tissue being treated, and partly to affect the transmission pattern for microwave energy into that tissue. The tip 24 also forms a water tight seal to the internal volume of the shaft 22.

The antenna assembly comprises a coaxial conductor 26 which extends along the inner volume of the shaft 22 from the first end $20_1$ towards the second end $20_2$. The coaxial conductor 26 is connectable, at a proximal end thereof, to the microwave energy generator 4 of FIG. 1. The coaxial conductor 26 comprises an inner conductor 28 of an electrically conductive material such as copper. Surrounding the inner conductor 28 is a dielectric layer 30 which extends along the inner conductor 28, radially outwardly thereof. The dielectric layer 30 is of any appropriate dielectric material. Surrounding the dielectric layer 30, is an outer conductor 32, which is of an electrically conductive material such as copper. The outer conductor 32 extends along an outer surface of the dielectric layer 30, radially outwards thereof. Typically, the inner conductor 28 is a wire having a circular cross section, such that the dielectric layer 30 is a cylinder of dielectric material surrounding an outer surface of the inner conductor 28. The outer conductor 32 is then formed by a cylinder of electrically conductive material surrounding an outer surface of the dielectric layer 30.

The dielectric layer 30 extends along the complete length of the inner conductor 28 to the distal end thereof. The outer conductor 32 stops short of the distal end of the inner conductor 28 and dielectric layer 30, and so is spaced apart longitudinally from that end point. The distal end of the coaxial conductor thereby defines a signal feed-point 34.

A dipole antenna element 36 extends longitudinally from the distal end (i.e. from the signal feedpoint 34) of the coaxial conductor 36 into a reception recess 38 in the applicator tip 24. The dipole antenna element 36 is connected to receive microwave energy from a microwave energy source by the coaxial conductor 26. The dipole antenna element 36 is arranged to emit microwave energy in a predetermined output pattern.

The reception recess 38 of the applicator tip 24 is located centrally with respect to the longitudinal axis of the assembly within the applicator tip 24. The reception recess 38 is designed so as to locate centrally the dipole tip portion 36 in the tip 24. The tip material is chosen for it mechanical and electrical properties, which have to be considered in the design.

In the example shown in FIG. 2, an electromagnetic choke assembly 40 is located within the shaft 22, around the coaxial conductor 26, spaced apart from the distal end of the coaxial conductor 26. It will be readily understood that the choke assembly is optional, depending on the design requirements of the assembly. The choke assembly 40 comprises a choke dielectric element 42 which extends around a portion of the outer conductor 32. In the case when the coaxial conductor 26 has a circular cross section, the choke dielectric element 42 is in the form of a cylinder of dielectric material surrounding an outer surface of the outer conductor 32 of the coaxial conductor 26. The choke dielectric has a proximal end towards the first end $20_1$ of the shaft 22 and a distal end towards the second end $20_2$ of the shaft 22. The length of the choke dielectric element 42 along the coaxial conductor 26 is determined by the desired electromagnetic/electrical characteristics of the choke assembly 40.

A dielectric fluid may be provided within the inner volume of the shaft 20 in order to provide a dielectric element in the microwave design and also provide a cooling fluid for the antenna assembly. This fluid may be isotonic saline or deionised water.

Figure 3:
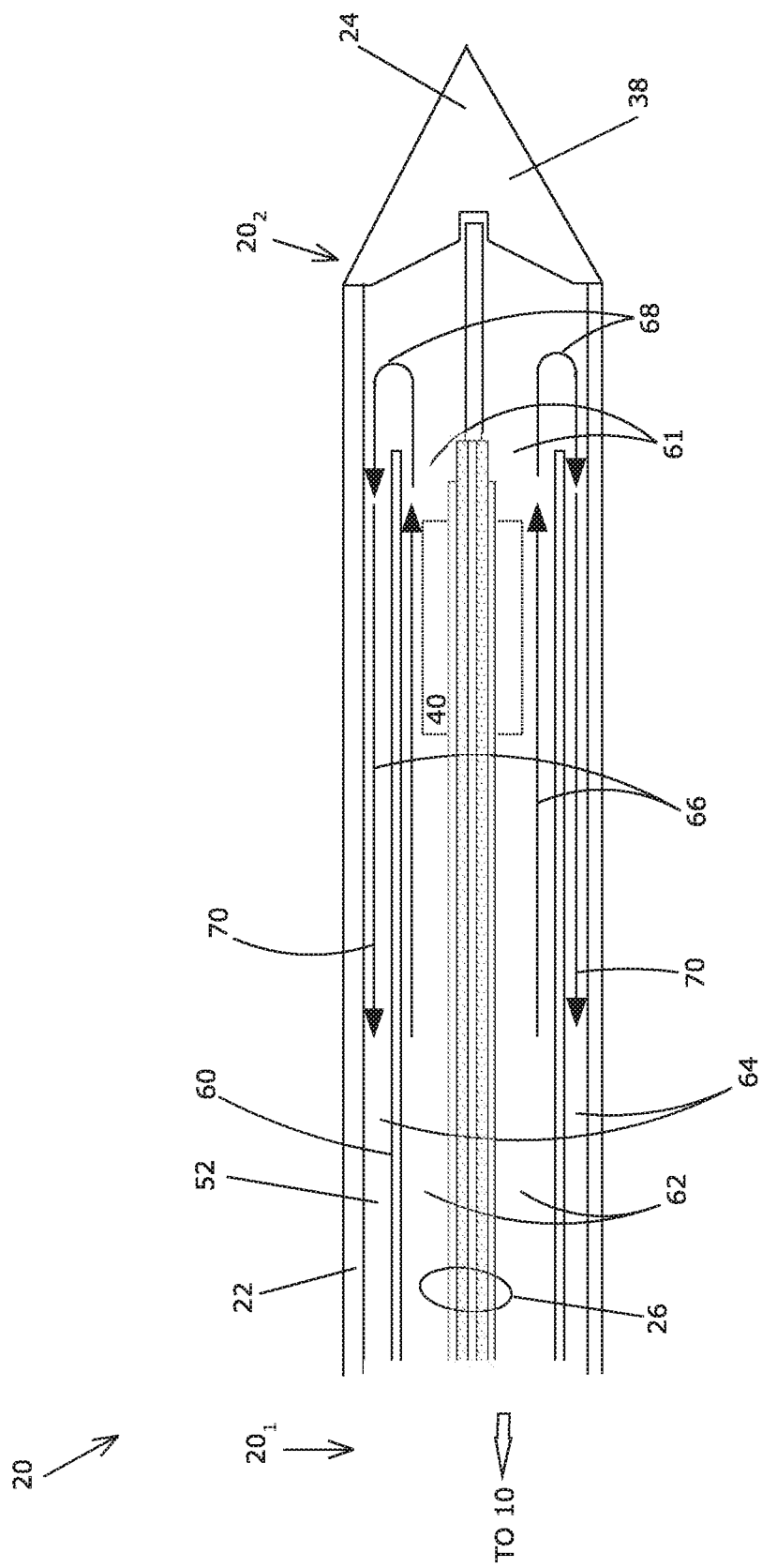
FIG. 3 is a cross sectional side view of a microwave ablation applicator including a coolant delivery tube.

FIG. 3 illustrates a cross sectional side view of an applicator 20 that includes a coolant delivery tube 60 for delivery of a coolant fluid, such as a dielectric coolant fluid, to the applicator tip 24. The coolant delivery tube 60 is coaxial with the shaft 22 and extends along the inner volume of the shaft 22. The coolant delivery tube 60 has a side wall which defines an elongate hollow interior of the coolant delivery tube having a first end towards the first end $20_1$ of the shaft 22 for reception of coolant fluid 52 therein, and a second end 61 towards, and spaced from, the second end $20_2$ of the shaft 22. The second end 61 of the coolant delivery tube 60 is at least partially open and defines a fluid flow path from the interior 62 of coolant delivery tube 60 into the inner volume of the shaft 22 adjacent the applicator tip 24.

The fluid flow path has a first portion 66 that extends along the interior of the coolant delivery tube 60, a second portion 68 that extends into the inner volume of the shaft adjacent the applicator tip 24 and antenna of the applicator 20. The second portion 68 of the fluid flow path extends back towards the first end of the coolant delivery tube, in a return volume 64 between an outer surface of the side wall of the coolant delivery tube 60 and an inner surface of the shaft 22. The fluid flow path then has a third portion 70 that extends along the return volume 64.

In use, coolant fluid is pumped into the hollow interior of the coolant delivery tube, so that the fluid flows along the fluid flow path. The fluid flow along the first, second and third portions 66, 68, 70 of the fluid flow path, back to a pump which recirculates the fluid. The pump may also provide cooling of the returning fluid. In such a manner, the applicator tip 24 of the applicator 20 can be cooled by the provision of coolant. However, such a design of coolant tube may lead to overcooling of the applicator tip 24, and/or to undercooling of the shaft 20.

Figure 4:
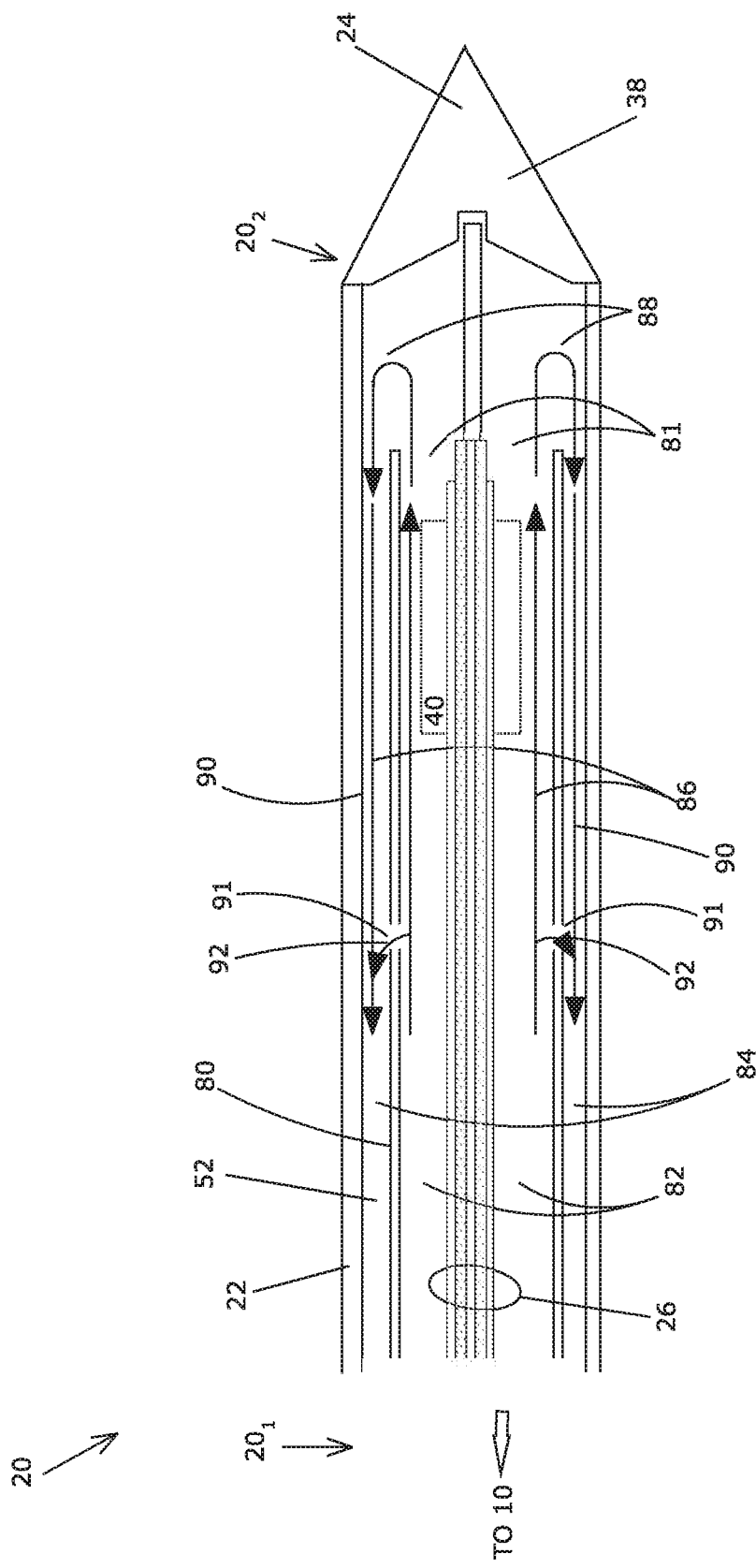
FIG. 4 is a cross sectional side view of a microwave ablation applicator embodying an aspect of the present invention.

Accordingly, an embodiment of the present invention seeks to provide improved control of cooling in an applicator. FIG. 4 illustrates a cross sectional side view of an applicator 20 embodying the principles of the present invention. The example of FIG. 4 includes a substantially rigid coolant delivery tube 80 for delivery of a coolant fluid, such as a dielectric coolant fluid, to the applicator tip 24. The coolant delivery tube 80 is coaxial with the shaft 22 and extends along the inner volume of the shaft 22. The coolant delivery tube 80 has a side wall which defines an elongate hollow interior of the coolant delivery tube having a first end towards the first end 20$_1$ of the shaft 22 for reception of coolant fluid 52 therein, and a second end 81 towards, and spaced from, the second end 20$_2$ of the shaft 22. The second end 81 of the coolant delivery tube 80 is at least partially open and defines a first fluid flow path from the interior 82 of coolant delivery tube 80 into the inner volume of the shaft 22 adjacent the applicator tip 24.

The first fluid flow path has a first portion 86 that extends along the interior of the coolant delivery tube 80, a second portion 88 that extends into the inner volume of the shaft adjacent the applicator tip 24 and antenna of the applicator 20. The second portion 88 of the fluid flow path extends back towards the first end of the coolant delivery tube, in a return volume 84 between an outer surface of the side wall of the coolant delivery tube 80 and an inner surface of the shaft 22. The first fluid flow path has a third portion 90 that extends along the return volume 64.

The coolant delivery tube 80 also defines at least one return aperture 91 through the side wall thereof. The aperture 91 is of fixed size, and is located between the first and second ends of the coolant delivery tube 80 within the shaft 22, and provides a second fluid flow path 92 from the interior 82 of the coolant delivery tube 80 into the return volume 84. The coolant delivery tube 80 may be provided with any appropriate number of return apertures 91, and these may be sized and arranged as appropriate to control the relative flow rates of coolant along the first and second fluid flow paths 86, 88, 90 and 92. In one example, a plurality of apertures 91 may be arranged around the side wall of the coolant delivery tube 80, the return apertures 91 being spaced apart from one another evenly around the tube 80.

The return apertures 91 may be arranged in an appropriate pattern. For example, the return apertures 91 may be arranged in a plane substantially perpendicular to the longitudinal axis of the shaft 22. Alternatively, the return apertures 91 may be arranged in spiral pattern along a portion of the coolant delivery tube 80, or may be distributed therealong in another pattern.

The relative flow rates of coolant along the first and second fluid flow paths determines the amount of cooling experience by different parts of the applicator 20. For example, larger return apertures 91 results in higher flow through along the second fluid flow path, and lower flow along the first fluid flow path. This arrangement then leads to lower cooling at the applicator tip 24 compared to the remainder of the shaft 22 of the applicator 20. This control allows for a desired temperature distribution to be achieved, and to reduce temperatures outside of the region being treated by the application of microwave energy. Such reduced temperatures outside of the treatment region can reduce the occurrence of unwanted tissue ablation and damage.

In use, coolant fluid is pumped into the hollow interior 82 of the coolant delivery tube 80, so that the fluid flows along the first and second fluid flow paths 86, 88, and 90, and 92. The fluid flows back to a pump which recirculates the fluid. The pump may also provide cooling of the returning fluid. In such a manner, the applicator tip 24 and shaft 22 of the applicator 20 can be cooled in a desired pattern and manner.

The invention claimed is:

1. A shaft assembly for a microwave ablation applicator which includes the shaft assembly and an antenna assembly located within the shaft assembly, the shaft assembly comprising: an elongate shaft which extends from a first end to a second end thereof, and which defines a longitudinal axis of the antenna assembly; an applicator tip mounted on the second end of the elongate shaft; and a coolant delivery tube, for housing the antenna assembly, comprising a single thickness side wall which defines an elongate hollow interior, the single thickness side wall and elongate shaft defining a return volume therebetween, the coolant delivery tube extending along an inner volume of the elongate shaft, coaxial therewith, the coolant delivery tube having a first end towards the first end of the elongate shaft for reception of coolant fluid therein, and a second end towards, and spaced from, the second end of the elongate shaft, the second end of the coolant delivery tube providing a first fluid flow path from the interior of the coolant delivery tube into the inner volume of the elongate shaft via a distal axial opening adjacent the applicator tip and into the return volume, wherein the coolant delivery tube defines a return aperture through the side wall thereof, which return aperture is of a fixed size and is located between the first and second ends of the coolant delivery tube within the elongate shaft and is spaced from the second end of the coolant delivery tube, and which return aperture provides a non-closable second fluid flow path from the interior of the coolant delivery tube into the return volume, which non-closable second fluid flow path is spaced apart from the second end of the coolant delivery tube.

2. An assembly as claimed in claim 1, wherein the coolant delivery tube defines a plurality of such return apertures through the side wall thereof.

3. An assembly as claimed in claim 1, wherein the coolant delivery tube defines a plurality of such return apertures through the side wall thereof, which return apertures are spaced apart circumferentially around the side wall of the coolant delivery tube.

4. An assembly as claimed in claim 1, wherein the coolant delivery tube defines a plurality of such return apertures through the side wall thereof which return apertures are arranged in a plane substantially perpendicular to the longitudinal axis of the shaft.

5. A microwave ablation applicator comprising a shaft assembly and an antenna assembly located within the shaft assembly, the shaft assembly comprising:
an elongate shaft which extends from a first end to a second end thereof, and which defines a longitudinal axis of the antenna assembly;
an applicator tip mounted on the second end of the elongate shaft; and
a coolant delivery tube comprising a single thickness side wall which defines an elongate hollow interior, the single thickness side wall and elongate shaft defining a return volume therebetween, the coolant delivery tube extending along an inner volume of the elongate shaft, coaxial therewith, the coolant delivery tube having a first end towards the first end of the elongate shaft for reception of coolant fluid therein, and a second end towards, and spaced from, the second end of the elongate shaft, the second end of the coolant delivery tube providing a first fluid flow path from the interior of the coolant delivery tube into the inner volume of the elongate shaft via a distal axial opening adjacent the applicator tip and into the return volume,
wherein the coolant delivery tube defines a return aperture through the side wall thereof, which return aperture is of a fixed size and is located between the first and second ends of the coolant delivery tube within the elongate shaft and is spaced from the second end of the coolant delivery tube, and which return aperture provides a non-closable second fluid flow path from the interior of the coolant delivery tube into the return volume, which non-closable second fluid flow path is spaced apart from the second end of the coolant delivery tube; and the antenna assembly including an elongate coaxial conductor for connection to a source of microwave energy, the coaxial conductor extending from the first end of the elongate shaft of the shaft assembly towards the second end of the elongate shaft through the interior of the coolant delivery tube, the coaxial conductor having an inner conductor, a dielectric layer arranged radially outwardly of the inner conductor and extending along the inner conductor, and an outer conductor arranged radially outwardly of the dielectric layer and extending along the dielectric layer, the inner conductor defining a signal feed-point of the coaxial conductor at a distal end thereof towards the second end of the elongate shaft, and a dipole tip portion which extends from the feed-point of the coaxial conductor towards the applicator tip of the shaft assembly, and which is electrically connected with the inner conductor of the coaxial conductor.

6. A microwave ablation applicator as claimed in claim 5, wherein the coolant delivery tube defines a plurality of such return apertures through the side wall thereof.

7. A microwave ablation applicator as claimed in claim 5, wherein the coolant delivery tube defines a plurality of such return apertures through the side wall thereof, which return apertures are spaced apart circumferentially around the side wall of the coolant delivery tube.

8. A microwave ablation applicator as claimed in claim 5, wherein the coolant delivery tube defines a plurality of such return apertures through the side wall thereof which return apertures are arranged in a plane substantially perpendicular to the longitudinal axis of the elongate shaft.

* * * * *